United States Patent [19]

Beech, Jr. et al.

[11] Patent Number: 4,751,339
[45] Date of Patent: Jun. 14, 1988

[54] ZEOLITE CATALYSIS PROCESS FOR CONVERSION OF DIENE-CONTAINING OLEFINS TO AROMATIC HYDROCARBONS

[75] Inventors: James H. Beech, Jr., Wilmington, Del.; Samuel A. Tabak, Wenonah, N.J.

[73] Assignee: Mobil Oil Corporation, New York, N.Y.

[21] Appl. No.: 6,089

[22] Filed: Jan. 23, 1987

[51] Int. Cl.$^4$ .............................................. C07C 12/02
[52] U.S. Cl. ..................................... 585/415; 585/533
[58] Field of Search ................................ 585/533, 415

[56] References Cited

U.S. PATENT DOCUMENTS

| | | | |
|---|---|---|---|
| 3,843,740 | 10/1974 | Mitchell | 260/673 |
| 4,052,477 | 10/1977 | Ireland et al. | 585/517 |
| 4,070,411 | 1/1978 | Butter et al. | 585/530 |
| 4,097,367 | 6/1978 | Haag et al. | 208/135 |
| 4,100,218 | 7/1978 | Chen et al. | 585/533 |
| 4,254,295 | 3/1981 | Tabak | 585/533 |
| 4,417,086 | 11/1983 | Miller | 585/530 |
| 4,417,087 | 11/1983 | Miller | 585/530 |
| 4,517,396 | 5/1985 | Hoek et al. | 585/415 |
| 4,542,248 | 9/1985 | Lucien | 585/417 |
| 4,547,616 | 10/1985 | Avidan et al. | 585/640 |
| 4,605,807 | 8/1986 | Mazurek | 585/517 |

FOREIGN PATENT DOCUMENTS 2156381 3/1985 United Kingdom.

*Primary Examiner*—Curtis R. Davis
*Attorney, Agent, or Firm*—Alexander J. McKillop; Michael G. Gilman; L. G. Wise

[57] ABSTRACT

A technique for continuous conversion of diene-containing aliphatic hydrocarbon feedstock to heavier hydrocarbon products wherein the feedstock is contacted at elevated temperature under endothermic high severity reaction conditions with a fluidized bed of acidic zeolite fine catalyst particles, comprising methods and means for:

maintaining the fluidized catalyst bed in a vertical reactor having a turbulent reaction zone by passing vapor upwardly through the reaction zone at a velocity greater than dense bed transition velocity to a turbulent regime and less than transport velocity for the average catalyst particle;

feeding a continuous stream of feedstock into the reaction zone, said feedstream comprising sufficient $C_3+$ alkanes to require net endothermic reaction conditions;

withdrawing a portion of coked catalyst from the reaction zone, oxidatively regenerating the withdrawn catalyst, heating the catalyst substantially above process temperature in the fluidized bed reactor, and returning hot regenerated catalyst to the reaction zone at a rate to control catalyst activity and reaction temperature under conditions of reaction severity to effect feedstock conversion to an aromatics-rich hydrocarbon effluent stream; and separating an aromatics-rich product from the fluidized bed effluent stream.

Aromatics yield is increased by recovering a recycle stream comprising $C_5+$ aliphatic hydrocarbons from the fluidized bed effluent stream for further conversion in the fluidized bed to increase aromatics product yield.

10 Claims, 1 Drawing Sheet

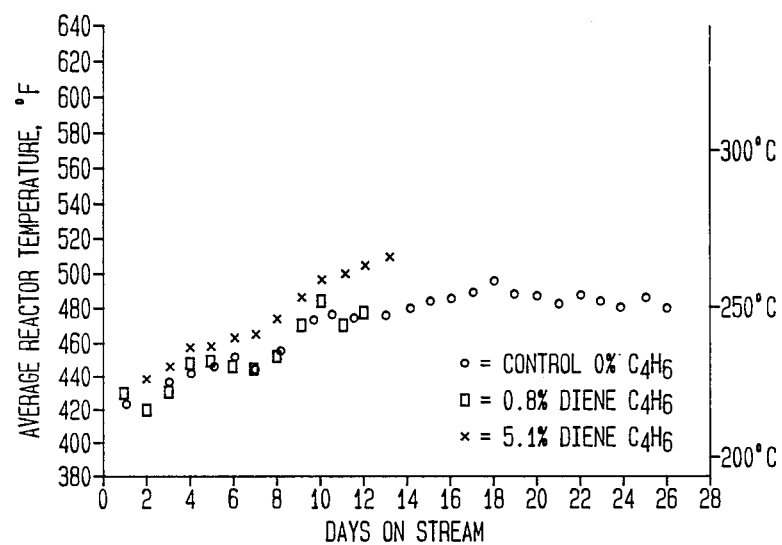

ZEOLITE CATALYSIS PROCESS FOR CONVERSION OF DIENE-CONTAINING OLEFINS TO AROMATIC HYDROCARBONS

BACKGROUND OF THE INVENTION

This invention relates to a catalytic technique for upgrading olefin streams rich in dienes to heavier hydrocarbons rich in aromatics. In particular, it provides a catalytic process for oligomerizing a feedstock containing monoalkenes and dienes to produce $C_5+$ hydrocarbons rich in $C_6$-$C_{10}$ aromatics, such as benzene, toluene, xylenes, tri- and tetramethyl benzenes, along with fuels and other useful products. Diene-containing liquids, such as thermal cracking byproduct, are useful feedstocks herein.

Developments in zeolite catalysts and hydrocarbon conversion processes have created interest in utilizing olefinic feedstocks for producing $C_5+$ gasoline, diesel fuel, etc. In addition to basic chemical reactions promoted by ZSM-5 type zeolite catalysts, a number of discoveries have contributed to the development of new industrial processes. These are safe, environmentally acceptable processes for utilizing feedstocks that contain olefins. Conversion of $C_2$-$C_4$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the ZSM-5 type zeolite catalysts. In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062, 4,211,640 and 4,227,992. The above-identified disclosures are incorporated herein by reference.

Conversion of olefins, especially alpha-monoalkenes such as propene and butenes, over HZSM-5 is effective at moderately elevated temperatures and pressures. The conversion products are sought as liquid fuels, especially the $C_5+$ aliphatic and aromatic hydrocarbons. Product distribution for liquid hydrocarbons can be varied by controlling process conditions, such as temperature, pressure and space velocity. Aromatic gasoline ($C_5$-$C_{10}$) is readily formed at elevated temperature (e.g., about 425° to 650° C.) and moderate pressure from ambient to about 5500 kPa, preferably about 200 to 2900 kPa. Olefinic gasoline can also be produced and may be recovered as a product or fed to a low severity, high pressure reactor system for further conversion to heavier distillate range products or otherwise utilized. Operating details for typical "MOGD" oligomerization units are disclosed in U.S. Pat. Nos. 4,456,779; 4,497,968 (Owen et al.) and 4,433,185 (Tabak), incorporated herein by reference.

Many feedstocks of commercial interest, such as thermal cracking byproduct, etc., contain both mono-olefins and diolefins (e.g. $C_2$-$C_6$ mono-alkenes and $C_4+$ dienes) along with light alkanes and aromatics. Gaseous and liquid streams containing dienes are typically produced in thermal cracking operations. One common example is pyrolysis gasoline which is produced as ethane (ethylene) cracking byproduct. Such diene-containing streams are often difficult to process due to poor thermal stability and the tendency of dienes to form coke and gum deposits. This complicates preheating of such streams into the high temperatures required of most catalytic upgrading processes. Prior attempts to upgrade such materials have pretreated the feedstock to hydrogenate the dienes selectively, as in U.S. Pat. No. 4,052,477 (Ireland et al). The present invention is concerned with providing a safe and low cost alternative to catalytically converting olefinic streams to high value $C_5+$ products, rich in aromatic hydrocarbons, including monocyclic benzenoids having 6 to 8 carbon atoms. The inventive process may be employed in converting paraffinic feedstocks containing diene components under aromatization reaction conditions.

SUMMARY OF THE INVENTION

A process has been discovered for converting lower olefinic hydrocarbon feedstock to aromatics-rich product by contacting the feedstock with acidic siliceous zeolite conversion catalyst particles at elevated temperature under aromatization conditions to produce heavier hydrocarbons including aromatic hydrocarbons. The improvement comprises introducing lower olefinic feedstock comprising at least one $C_4$-$C_6$ diene component into a bed of catalyst particles to convert feedstock to heavier hydrocarbon rich in aromatics; separating an aromatics-rich $C_5+$ liquid stream from fluidized bed reaction effluent; extracting aromatics components from the liquid stream and recovering a product stream comprising at least 50 wt% $C_6$-$C_8$ aromatic hydrocarbons.

THE DRAWING

The drawing is a graphic plot of reactor temperature vs operating time on stream, depicting aging rates and temperature to achieve constant conversion.

DESCRIPTION OF PREFERRED EMBODIMENTS

Description of Catalysts

Recent developments in zeolite technology have provided a group of medium pore siliceous materials having similar pore geometry. Most prominent among these intermediate pore size zeolites in ZSM-5, which is usually synthesized with Bronsted acid active sites by incorporating a tetrahedrally coordinated metal, such as Al, Ga, B, Fe or mixtures thereof, within the zeolitic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity (alpha value) of about 10-250, preferably about 10 to 80 based on total catalyst weight. In the fluidized bed reactor the coked catalyst may have an apparent activity (alpha value) of about 10 to 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, ZSM-38, and ZSM-48. Aluminosilicate ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245 and 4,046,839; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified if desired to adjust acidity and aromatization characteristics. A typical zeolite catalyst component having Bronsted acid sites may consist essentially of aluminosilicate ZSM-5 zeolite with 5 to 95 wt.% silica and/or alumina binder.

These siliceous zeolites may be employed in their acid forms ion exchanged or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (eg, ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone.

Certain of the ZSM-5 type medium pore shape selective catalysts are sometimes known as pentasils. In addition to the preferred aluminosilicates, the borosilicate, ferrosilicate and "silicalite" materials may be employed. ZSM-5 type pentasil zeolites are particularly useful in the process because of their regenerability, long life and stability under the extreme conditions of operation. Usually the zeolite crystals have a crystal size from about 0.01 to 2 microns or more.

Process Operation

In this description, metric units and parts by weight are employed unless otherwise stated.

Suitable olefinic feedstocks comprise $C_4$–$C_6$ alkenes including conjugated dienes such as 1,3-butadiene, pentadiene isomers, hexadienes, cyclic dienes, or similar $C_4+$ aliphatic liquid hydrocarbons having diethylenic conjugated unsaturation. Aromatics coproduced with the liquid olefinic components may be cofed or separated by solvent extraction prior to conversion of the diene-rich feedstock. Non-deleterious components, such as $C_1$–$C_2$ lower paraffins and inert gases, may be present. A particularly useful feedstock is a liquid by-product of pyrolysis or thermal cracking units containing typically 40-95 wt % $C_4$–$C_6$ total mono-olefins and di-olefins, including about 5-60 wt.% diene, along with varying amounts of $C_3$–$C_8$ paraffins, aromatics and inserts. Specific examples are given in the examples. The process may be tolerant of a wide range of total alkanes, from 0 to 95%. Preferred pyrolysis feedstocks may contain more than 50 wt.% $C_4$–$C_6$ lower aliphatic hydrocarbons, and contain sufficient olefins to provide a total olefinic partial pressure of at least 50 kPa. Under the high severity reaction conditions employed in the present invention, the $C_3$–$C_8$ lower alkanes are partially converted to heavier hydrocarbons.

The reaction severity conditions can be controlled to optimize yield of $C_6$–$C_8$ BTX hydrocarbons. It is understood that aromatics and light paraffin production is promoted by those zeolite catalysts having a high concentration of Bronsted acid reaction sites. Accordingly, an important criterion is selecting and maintaining catalyst inventory to provide either fresh or regenerated catalyst having the desired properties. Typically, acid cracking activity (alpha value) can be maintained from high activity values greater than 200 to significantly lower values under steady state operation by controlling catalyst deactivation and regeneration rates to provide an apparent average alpha value below 200, preferably about 10 to 80.

Reaction temperatures and contact time are also significant factors in the reaction severity, and the process parameters are followed to give a substantially steady state condition wherein the reaction severity index (R.I.) is maintained within the limits which yield a desired weight ratio of propane to propene. While this index may vary from about 0.2 to 200, it is preferred to operate the steady state fluidized bed unit to hold the R.I. below about 50, with optimum operation at 0.7 to 2 in the substantial absence of added propane. The optimal value will depend upon the exact catalyst composition, feedstock and reaction conditions; however, the typical diene-rich feed mixtures used in the examples herein and additional olefinic feeds can be optionally upgraded to the desired aliphatic-rich gasoline by keeping the R.I. at about 1. While reaction severity is advantageously determined by the weight ratio of propane:propene in the gaseous phase, it may also be approximately by the analogous ratios of butanes:butenes, pentanes:pentenes, or the average of total reactor effluent alkanes:alkenes in the $C_3$–$C_5$ range. Accordingly, these alternative expressions may be a more accurate measure of reaction severity conditions when propane is added to the feedstock.

Upgrading of olefins by such hydrogen contributors in fluidized bed cracking and oligomerization units is taught by Owen et al in U.S. Pat. No. 4,090,949. This technique is particularly useful for operation with a pyrolysis cracking unit to increase overall production of liquid product. In a typical process, the diene-rich $C_4+$ olefinic feedstock is converted in a catalytic reactor under oligomerization conditions and moderate pressure (ie-100 to 2500 kPa) to produce a predominantly liquid product consisting essentially of $C_5+$ hydrocarbons rich in gasoline-range mono-olefins and aromatics.

The use of fluidized bed catalysis permits the conversion system to be operated at low pressure drop, which in an economically practical operation can provide a maximum operating pressure only 50 to 200 kPa above atmospheric pressure. Another important advantage is the close temperature control that is made possible by turbulent regime operation, wherein the uniformity of conversion temperature can be maintained within close tolerances, often less than 25° C.

This process can be used with any process stream which contains sufficient liquid olefins and dienes and is substantially free of deleterious oxygenates and sulfur compounds. Experimental runs are performed using a ZSM-5 catalyst to demonstrate the inventive process. The fluidized bed unit can be operated over a wide range of process variables and catalyst activity.

Reactor Operation

A typical reactor unit employs a temperature-controlled catalyst zone with indirect heat exchange and/or adjustable gas quench, whereby the reaction temperature can be carefully controlled to prevent excessive temperature above the usual operating range of about 200° C. to 650° C., preferably at average reactor temperature of 250° C. to 580° C. Energy conservation in the system may utilize at least a portion of the reactor exotherm heat value by exchanging hot reactor effluent with feedstock and/or recycle streams. Optional heat exchangers may recover heat from the effluent stream prior to fractionation. It is preferred to operate the olefin conversion reactor at a total pressure of about 100 to 6000 kPa (atmospheric to about 60 bars). The weight hourly space velocity (WHSV, based on total olefins in the fresh feedstock and total catalyst weight) usually is about 0.1–5 WHSV.

EXAMPLE 1

In the present example a $C_4^+$ liquid stream is converted to aromatics-rich gasoline in the fluidized bed reactor employing acid ZSM-5 powder catalyst having a fresh alpha value of about 10–80 at an average conversion temperature about 425° C. (800° F.) and total pressure of about 275 kPa (25 psig). The liquid pyrolysis gasoline feedstock contains about 22 wt.% $C_4^+$ monoalkenes, 27% $C_4^+$ dienes (mainly butadienes), 49% $C_4^+$ paraffins, 2% aromatics and naphthenes, and less than 1% $C_3^-$ aliphatics. Following initial heating and fluidization of the powdered catalyst with a heated lift gas (e.g. $C_2^-$ hydrocarbon), the feedstream is preheated and maintained below 180° C. prior to injection into the bed. After achieving steady state operation at a reaction severity index (R.I.) of about 2, the effluent conversion product (less any lift gas components) comprises 4.9% benzene (B), 11.8% toluene (T), 14.0% xylenes (X) and 0.9% ethyl benzene, 2.3% $C_9$ aromatics isomers and 0.5% $C_{10}$ isomers. The nonaromatic fraction contains mainly mono-olefins, paraffins and naphthenes, and the light gas $C_4^-$ fraction is 13.5% of the conversion product.

Comparative effluent streams for high severity and low severity conversion runs under steady state reactor conditions are shown in Table 1. The high severity example is run at 600° C., 0.87 WHSV, 1 bar (100 kPa) over HZSM-5. The low severity example is run at the same conditions, except at 425° C.

TABLE 1

| | EXAMPLE 1A | EXAMPLE 1B |
|---|---|---|
| Temperature (°C.) | 600 | 425 |
| Products Yield | High Severity | Low Severity |
| $H_2$, wt. % | 3.0 | 1.3 |
| $C_1$ | 13.5 | 2.6 |
| $C_2$ | 10.3 | 6.1 |
| $C_3$ | 3.8 | 3.4 |
| $C_4^+$ | 2.0 | 1.4 |
| $C_5$ Non-Aromatic | — | 50.3 |
| Benzene | 22.1 | 4.9 |
| Toluene | 21.9 | 11.8 |
| Ethyl Benzene | 0.9 | 0.9 |
| Xylene | 15.6 | 14.0 |

TABLE 1-continued

| | EXAMPLE 1A | EXAMPLE 1B |
|---|---|---|
| $C_9$ Aromatics | 2.7 | 2.3 |
| $C_{10}^+$ | 3.2 | 0.5 |
| Coke | 1.0 | 0.5 |
| | 100.0 | 100.0 |

EXAMPLES 2–4

A series of continuous olefin conversion runs are conducted under oligomerization conditions to upgrade mixtures of ethene, propene, butene and butadiene and to determine the effects of diene concentration on catalyst aging. The control feedstock (Example 2) is compared with diene-containing feeds in Table 2.

TABLE 2

| | Example 2 | Example 3 | Example 4 |
|---|---|---|---|
| Ethene | 0 | 0.7 | 1.8 |
| Propene | 26.8 | 28.1 | 22.9 |
| Butenes | 35.7 | 31.9 | 31.7 |
| 1,3 Butadiene | 0 (control) | 0.8 | 5.1 |
| Alkanes ($C_4^-$) | 37.5 | 38.5 | 38.5 |
| Recycle (mol/mol olefin) | 2.5:1 | 2.5:1 | 2.5:1 |

The conversion unit is a single bed isothermal reactor employing acid ZSM-5 having a crystal size less than 0.5 microns, together with 35% alumina binder and having a fresh alpha value of about 175. The continuous runs are conducted at about 6600 kPa and weight hourly space velocity (WHSV) of about 0.8 parts olefin feed per part by weight of catalyst per hour. The conversion runs are started at 205° C. (400° F.) and the temperature is increased to compensate for coke deposition, while maintaining total olefin conversion of at least 80%, preferably over 90%. Results of the aging studies are plotted in FIG. 3, with all conversion rates being normalized to 80% conversion to 330° F.+ for comparison purposes. Selectivity of the conversion product to heavier hydrocarbons is shown in Table 3.

TABLE 3

| | Example 2 | Example 3 | Example 4 |
|---|---|---|---|
| Total Liquid Product, 50% pt, °C. (°F.) | 261/(501) | 259/(498) | 244/(472) |
| Distillate Species (As Cut) | | | |
| 5 wt. %, °C. (°F.) | 232/(434) | 250/(483) | 297(477) |
| 95 wt. % °C. (°F.) | 369/(697) | 383/(722) | 379(715) |
| Gravity, °API | 44.3 | 41.2 | 38.9 |
| Aniline Point | 177 | 184 | 172 |

While the aromatics product content of the control runs averaged about 2–5%, the 5.1% butadiene feed (Example 4) is upgraded to an aromatics content of 15.5 wt.%, more than 3 times the diene input. Prior processes for converting olefins to monocyclic $C_6$–$C_8$ benzenoids require high temperature to produce the aromatics in good yield. Accordingly, it is an unexpected result that the experimental runs from about 200° C. increase the aromatics yield by addition of the diene. The average paraffin content is less than 14% and the liquid dominant product is 70%+olefins and naphthenes.

These results indicate butadiene, at levels of 1 wt.% or less, do not cause significantly increased catalyst aging or lower product selectivity. Typical FCC $C_3$/$C_4$ olefins from a depropanizer feed stream contain 0.2–0.6 wt.% butadiene which is less than the 0.8 wt.% butadiene concentration used in this study. Even at the 5.1 wt.% butadiene level, though catalyst aging is increased, product selectivity to heavier hydrocarbons remained relatively high.

Typical olefinic pyrolysis byproduct streams are shown in Table 4.

TABLE 4

Example of Diene-Rich Feestock (ethane cracking byproduct)

| Component | Vol. % |
|---|---|
| $C_3^-$ | 1.0 |
| i-butene | 0.08 |
| 1,3-butadiene | 0.51 |
| t.2,butene | 0.1 |
| c.2,butene | 0.15 |
| 1,2 butadiene | 0.14 |
| 3m 1 butene | 0.45 |
| isopentane | 5.44 |
| 1,4 pentadiene | 0.6 |
| 1-pentene | 0.63 |
| n-pentane | 1.92 |
| isoprene | 2.3 |
| c,2,pentene | 0.35 |
| 2m2butene | 0.45 |
| t,1,3, pentadiene | 1.5 |
| c,1,3,pentadiene | 1.0 |
| cyclopentadiene | 13.7 |
| cyclopentene | 1.7 |
| 2,3 d.m. butane | 1.7 |
| 3mpentene | 0.85 |
| hexane | 0.95 |
| unknown $C_6$ | 1.04 |
| cyclohexane | 3.06 |
| benzene | 34.4 |
| unknown $C_8$ | 3.47 |
| Toluene | 10.1 |
| vinyleydohexene | 0.19 |
| ethylbenzene | 1.29 |
| xylene | 1.01 |
| styrene | 0.3 |
| unknown $C_9^+$ | 6.9 |

The above diene-rich stream example contains $C_6^+$ aromatic hydrocarbons which can be separated before feeding to the reactor. Typical ranges of diene-rich pyrolysis gasoline streams comprised of mainly $C_4$-$C_6$ hydrocarbons are:

|  | Vol. % |
|---|---|
| Dienes | 5–60 |
| Mono-alkenes | 5–30 |
| Aromatics | 1–5* |
| Alkanes | 20–60 |
| Naphthenes | 1–5 |

*can be as high as 60% if $C_6^+$ fraction is not separated.

The flexibility of the fluid bed operating parameters for controlling the reactor temperature under exothermic reaction conditions allows an easy adjustment for achieving the optimal yield structure.

In order to effect fluidization of the catalyst at the bottom of the reactor prior to injection of the liquid feed stream, a lift gas may be employed. This can be an inert diluent or recycled light gas, such as methane, ethane, ethene, propane, etc. Recycle of $C_3^-$ light hydrocarbons may also be desirable under certain circumstances, for instance with unreacted aliphatics which require further conversion. The thermodynamic balance of exothermic olefin oligomerization and endothermic paraffin reactions can have significant impact on the reaction severity conditions.

The use of a fluid-bed reactor in this process offers several advantages over a fixed-bed reactor. Due to continuous catalyst regeneration, fluid-bed reactor operation will not be adversely affected by oxygenate, sulfur and/or nitrogen containing contaminants present in the pyrrolysis byproduct.

While the invention has be shown by describing preferred embodiments of the process, there is no intent to limit the inventive concept, except as set forth in the following claims:

We claim:

1. A process for converting lower olefinic hydrocarbon feedstock to aromatics-rich product by contacting the feedstock with acidic siliceous zeolite conversion catalyst particles at elevated temperature between about 200 degrees C. to 650 degrees C. under aromatization conditions to produce heavier hydrocarbons including aromatic hydrocarbons comprising:

introducing lower olefinic feedstock comprising at least one $C_4$-$C_6$ diene component into a bed of catalyst particles to convert feedstock to heavier hydrocarbon rich in aromatics;

separating an aromatics-rich $C_5^+$ liquid stream from fluidized bed reaction effluent;

extracting aromatics components from the liquid stream and recovering a product stream comprising at least 50 wt% $C_6$-$C_{10}$ aromatic hydrocarbons.

2. The process of claim 1 wherein the olefinic feed comprises about 5 to 90 wt.% $C_4^+$ mono-olefin and 1 to 50 wt.% conjugated unsaturated diolefins; and wherein the net yield of aromatic product comprises at least 15 wt% of the olefin components of the feedstock.

3. The process of claim 2 wherein said feedstock consists essentially of liquid pyrolysis gas byproduct of hydrocarbon pyrolysis, wherein the catalyst comprises zeolite having the crystalline structure of ZSM-5.

4. In the process for catalytic conversion of lower olefinic hydrocarbon feed to heavier hydrocarbons wherein the olefinic feedstock is contacted under conversion conditions at elevated temperature with an acidic medium pore shape selective metallosilicate catalyst, the improvement which comprises:

cofeeding at least one $C_2$-$C_4$ mono-alkene with at least one $C_4$-$C_6$ conjugated diene for concurrent conversion to an aromatics-rich $C_5^+$ liquid product at a temperature between about 200 degrees C. to 650 degrees C. whereby an improved yield of aromatics is produced.

5. The process of claim 4 wherein aromatics produced in the conversion are substantially greater than that produced by the equivalent mono-alkenes without diene cofeeding.

6. The process of claim 4 wherein the catalyst comprises aluminosilicate ZSM-5, the diene comprises 1,3-butadiene and the mono-alkenes comprises either, butene and/or propene.

7. The process of claim 5 wherein the aromatics content of $C_5^+$ liquid product is at least 15 wt.%.

8. In the process for producing benzenoid hydrocarbons from aliphatic hydrocarbon feed by contacting with a medium pore shape selective acid zeolite catalyst at elevated reaction temperature, the improvement which comprises feeding a conjugated di-ethylenically unsaturated diene with the aliphatic hydrocarbon feed under aromatization conditions between about 200 degrees C. and 650 degrees C. in an amount to increase $C_6$-$C_8$ monocyclic benzenoid production substantially above that produced by diene-free aliphatic feed.

9. The process of claim 8 wherein the feed consists essentially of aliphatic hydrocarbons having up to six carbon atoms, including about 5 to 50 wt.% diene and 5 to 95 wt.% mono-alkene; the reaction temperature is at about 200° C. to 650° C.; the catalyst comprises an aluminosilicate having the crystalline structure of ZSM-5; and reaction effluent contains at least 15 wt.% total $C_6$–$C_8$ benzenoid hydrocarbons.

10. The process of claim 8 wherein the reaction temperature is maintained in the range of about 200° to 650° C. at a partial olefin pressure of at least 50 kPa.

* * * * *